(12) United States Patent
Cummins

(10) Patent No.: US 6,372,218 B1
(45) Date of Patent: Apr. 16, 2002

(54) INTERFERON DOSAGE FORM AND METHOD THEREFOR

(75) Inventor: Joseph M. Cummins, Amarillo, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 08/381,136

(22) Filed: Jan. 31, 1995

Related U.S. Application Data

(63) Continuation of application No. 08/003,624, filed on Jan. 13, 1993, now abandoned, which is a continuation of application No. 07/775,291, filed on Oct. 9, 1991, now abandoned, which is a division of application No. 07/110,501, filed on Oct. 26, 1987, now abandoned, which is a continuation-in-part of application No. 06/927,834, filed on Nov. 6, 1986.

(51) Int. Cl.$^7$ .................. A61K 39/00; A61K 38/21; A61K 9/20; C07K 14/00
(52) U.S. Cl. ................ 424/184.1; 424/85.4; 424/85.5; 424/85.6; 424/85.7; 424/464; 530/351; 514/12
(58) Field of Search ............... 424/85.4, 85.5, 424/85.6, 85.7, 464, 184.1; 514/12; 530/351

(56) References Cited

U.S. PATENT DOCUMENTS

| | | | |
|---|---|---|---|
| 3,906,092 A | | 9/1975 | Hilleman et al. |
| 4,053,582 A | | 10/1977 | Stickl |
| 4,273,703 A | | 6/1981 | Osther et al. |
| 4,276,282 A | | 6/1981 | Sugimoto et al. |
| 4,460,574 A | | 7/1984 | Yabrov |
| 4,462,985 A | * | 7/1984 | Cummins .................. 424/85.4 |
| 4,465,702 A | | 8/1984 | Eastman et al. |
| 4,496,537 A | | 1/1985 | Kwan |
| 4,497,795 A | | 2/1985 | Cummins |
| 4,507,281 A | | 3/1985 | Asculai et al. |
| 4,605,555 A | | 8/1986 | Sato et al. |
| 4,670,252 A | * | 6/1987 | Sampathkumar ............. 424/53 |
| 4,675,184 A | * | 6/1987 | Hasegawa et al. ......... 424/85.4 |
| 4,946,674 A | | 8/1990 | von Eichborn et al. .... 424/85.5 |
| 5,002,970 A | * | 3/1991 | Eby ........................... 514/494 |
| 5,145,677 A | | 9/1992 | von Eichborn et al. .... 424/85.5 |
| 5,286,748 A | * | 2/1994 | Eby ........................... 514/494 |

FOREIGN PATENT DOCUMENTS

| | | |
|---|---|---|
| AU | A-48408/85 | 7/1985 |
| AU | 4841285 | 4/1986 |
| DE | 0180737 | 5/1986 |
| EP | 0107498 | 5/1984 |
| EP | 0177342 | 4/1986 |
| JP | 60-116631 | 6/1985 |
| WO | PCT/US81/01103 | 8/1981 |
| WO | WO 82/00588 | 3/1982 |
| WO | WO 83/01198 | 4/1983 |

OTHER PUBLICATIONS

Tompkins, *Feline Practice*, May/Jun. 1982 12:6–15.*
Solovi'ev, *World Health Org.* 41:683–388 (1969).*
Dunnick et al. *J. of Infect. Dis.* 139(1):109–123 (1979).*
Goodman et al. (Goodman), The Pharmacological Basis of Therapeutics, The MacMillan Co., New York, p. 9 (1965).*
Medline database, acc. No. 03189153, citing Miyoshi, T., et al. (1977) *Cancer* 40(6): 2999–3003. (Attached to office action).*
Rodder, H.; Thumann, D.; Thumann, E., *Tierarztliche Umschau*, 1979, vol. 34, No. 10, pp. 720–724 (summary).
Toneva, V., *Bulletin de l'Office International des Epizooties*, 1977, vol. 88, pp. 631–637 (summary).
Finter, N.B.; Oldham, R.R., (eds.), In Vivo and Clinical Studies, *Interferon*, 1985, vol. 4, pp. 137, 148, 173, 218, 226, 284, 285, 330.
Litvinov, A. N., *Chemical Abstracts*, 1967, vol. 67, p. 7536 [80070u].
Time and Dosage Dependence of Immunoenhancement by Murine Type II Interferon Preparations, *Cellular Immunology*, 1978, 40, pp. 285–293.
Stewart II, W.E.; Gottlieb, A.A. (eds.), *Interferons and Their Actions*, 1977, pp. 102–104.
Werenne, J.; Broecke, C.V.; Schwers, A.; Goossens, A.; Bugyaki, L.; et al., Antiviral Effect of Bacterially Produced Human Interferon (Hu–IFNa$_2$) Against Experimental Vaccinia Infection in Calves, *Journal of Interferon Research*, 1985, 5:129–136.
Roney, C.S., et al., Effect of Human Leukocyte A Interferon on Prevention of Infectious Bovine Rhinotracheitis Virus Infection of Cattle, *Am J. Vet. Res.*, Jun. 1985, vol. 46, No. 6, pp. 1251–1255.
Tompkins, M.B.; Cummins, J.M., Response of Feline Leukemia Virus–Induced Nonregenerative Anemia to Oral Administration of an Interferon–Containing Preparation, *Feline Practice*, May–Jun. 1982, vol. 12, No. 3, pp. 6–15.
Miller, B., Interferon Enters the Fray, *Farm Journal*, Oct. 1985, pp. 12–13.
Grob, P.J., et al., Interferon as an Adjuvant for Hepatitis B Vaccination in Non– and Low–Responder Populations, *Eur. J. Clin. Microbiol.*, Jun. 1984, vol. 3, No. 3, pp. 195–198.
Cummins, J.M.; Rosenquist, B.D., Protection of Calves Against Rhinovirus Infection by Nasal Secretion Interferon Induced by Infectious Bovine Rhinotracheitis Virus, *American Journal of Veterinary Research*, Feb. 1980, vol. 41, No. 2, pp. 161–165.

(List continued on next page.)

Primary Examiner—Yvonne Eyler
Assistant Examiner—Janet L. Andres
(74) Attorney, Agent, or Firm—Barnes & Thornburg

(57) ABSTRACT

Neoplastic disease, hyperallergenicity, autoimmune disorders characterized by chronic tissue degenerative inflammation and immuno-resistant viral infections are treated by the administration of interferon at a dosage of about 0.1 to about 5 IU/lb per day by contacting said interferon with oral/pharyngeal mucosa. Interferon is administered in solution or in a novel solid unitary dosage form adapted to be dissolved in saliva when placed in the mouth.

7 Claims, No Drawings

OTHER PUBLICATIONS

Loan, R.W. (ed.), Bovine Respiratory Disease—A Symposium, Texas A&M University Press, College Station, TX, 1984, pp. 484–485.

Greenberg, S.B.; Harmon, M.W.; Johnson, P.E., Activity of Exogenous Interferon in the Human Nasal Mucosa, *Texas Reports on Biology and Medicine*, 1977, vol. 35, pp. 491–496.

Merigan, T.C.; Hall, T.S.; Reed, S.E.; Tyrrell, D.A., Inhibition of Respiratory Virus Infection by Locally Applied Interferon, *The Lancet*, Mar. 17, 1973, pp. 563–567.

Tyrrell, D.A.J., Trials of Interferon in Respiratory Infections of Man, *Texas Reports on Biology and Medicine*, 1977, vol. 35, pp. 486–490.

Shalaby, M.R.; Weck, P.K., Bacteria–Derived Human Leukocyte Interferons After in Vitro Humoral and Cellular Immune Responses, 82, 1983, pp. 269–281.

Strander, H.; Cantell, K.; Carlstron, G.; Jakobsson, P.A., Clinical and Laboratory Investigations on Man: Systemic Administration of Potent Interferon to Man, *J. Natl. Cancer Inst.*, 1973, 51: 733–742.

Vlatkovic, R., et al., Application of Human Leukocyte Interferon in Severe Cases of Virus B Hepatitis, *Proc. Symposium on Interferon 1979*, Yugoslav Academy of Sciences and Arts, Zagreb, pp. 172–183.

Effect of Interferon on Vaccination in Volunteers, *The Lancet*, Apr. 28, 1962, pp. 873–875.

Oh, J.O.; Yoneda, C., Induction of Ocular Resistance to Vaccinia Virus by Typhoid Vaccine; Role of Interferon, *The Journal of Immunology*, 1969, vol. 102, No. 1, pp. 145–154.

Clinical Trails With Exogenous Interferon; Summary of a Meeting, *The Journal of Infectious Diseases*, Jan. 1979, vol. 139, No. 1, pp. 109–123.

Soloviev, V.D.; Geo. Rita (ed.), Some Results and Prospects in the Study of Endogenous and Exogenous Interferon, *The Interferson, An International Symposium*, Academic Press, 1968, pp. 233–243.

Influenza and Interferon Research in the Soviet Union—Jan. 1973, *The Journal of Infectitous Diseaese*, Aug. 1973, vol. 128, No. 2, pp. 261–264.

Solov'ev, V.D., The Results of Controlled Observations on the Prophlaxis of Influenza with Interferon *World Health Organization*, 1949, 41, 683–688.

Jia–xiong, D., et al., Children's Respiratory Viral Diseases Treated with Interferon Aerosol *Chinese Medical Journal*, 1987, 100 (2): 162–166.

Sommerville, R.G., Essential Clinical Virology, *Blackwell Scientific Publications*, pp. 154–157.

Davies, H.W. et al, Comparative Intranasal Pharmacokinetics of Interferon Using Two Spray Systems, *J. Interferon Research*, 1983, pp. 443–449.

Couch, R.B., The Common Cold Control? *The Journal of Infectitious Diseases*, Aug. 1984, vol. 150, No. 2, pp. 167–173.

Mandell, G.L.; Douglas, Jr., R.G.; Bennett, J.E. (eds.), *Principles and Practice of Infectious Diseases*, 2nd ed., A Wiley Medical publication, pp. 85–96, 863, 968.

Galasso, G.J.; T.C. Merigan; Buchanan, R.A., *Antiviral Agents and Viral Diseases of Man*, Raven Press, New York, 1979, pp. 407–408, 430–431.

Galasso, G.J.; T.C. Merigan; Buchanan, R.A., *Antiviral Agents and Viral Diseases of Man*, Raven Press, New York, 1984, pp. 145–178, 344–345.

*Interferon Perspective*, Information on interferon provided in 1981 by the International Preventative Medicine Foundation, Melbourne, FL, Ronald Jones, Vice President.

American Interhealth, Melbourne Beach, FL, Production Information.

Biovet International, Inc., Canine and Feline Interferons, 1981 Product Description and label.

*Agriferon®–C*, Immuno Modulators Laboratories, Inc., Stafford, TX, Lymphokine Preparation for Prophylactic Treatment of Infectious Bovine Rhinotracheitis Virus Associated With Shipping Fever–for cattle use in Texas only, product brochure.

*Agriferon®–C*, A Bold New Approach To Managing Shipping Fever In Cattle Immuno Modulator Laboratories, Inc., Stafford, TX, product advertisement.

*Equiferon*, A Totally New Approach To Viral Respiratory Infection In Horses Immuno Modulator Laboratories, Inc., Stafford, TX, product advertisement.

*Pet Interferon Alpha*, Lymphokine Preparation For Treatment of Feline Leukemia Virus and Canine Parvovirus Diseases, Amarillo Cell Culture Co., Inc., Amarillo, TX, product brochure.

Texas Department of Health Application for License for Human Interferon Alpha (Alpha Interferon) as *Pet Interferon*, Amarillo Cell Culture Company, Inc., May 6, 1985.

Cantel, K; Ryhala, L., Circulating Interferon in Rabbits After Administration of Human Interferon by Different Routes, *Journal of General Virology*, 1973, 20:97–104.

Wills, R.J.; Spiegel, H.E.; Soikel, K.F., Pharmacokinetics of Recombinant Alpha A Interferon Following IV Infusion and Bolus, IM and PO Administrations to African Green Monkeys, *Journal of Interferon Research*, 1984, vol. 4, No. 3, pp. 399–409.

Gibson, D.M., et al., Pharmacokinetics of Recombinant Leukocyte A Interferon Following Various Routes and Modes of Administration To the Dog, *Journal of Interferon Research*, 1985, 5:403–408.

Smerdel, S., et al., Stimulation of Humoral Immunity by Interferon, *III Mediterranean Congress of Chemotherapy*, Sep. 21–24, 1982 presentation, vol. 2, p. 132, Oct. 1983.

Braun, W.; Levy, H.B., Interferon Preparations as Modifiers of Immune Responses, *Proc. Soc. Exp. Biol. Med.*, 1972, vol. 141, pp. 769–773.

DeMaeyer, E., Interferon and the Immune System: A Review (Limited to Alpha and Beta Interferons), *The Biology of the Interferon System*, Elsevier/North–Holland Biomedical Press, 1981, pp. 203–209.

Vignauz, F., et al., Effect of Virus–Induced Interferon on the Antibody Response of Suckling and Adult Mice, *Eur. J. Immunol.*, 1980, vol. 10, pp. 767–772.

Ikic, D., et al, The clinical Use of Human Leukocyte Interferon In Viral Infections, *International Journal of Clinical Pharmacology, Therapy and Toxicology*, 1981, vol. 19, No. 11, pp. 498–505.

Salaj–Rakic, T., et al., Primjena Humanog Leukocitnog Interferona U Male Djece Sa Gingivostomatitisom, *Proceedings–Yougoslav–Pediatric Congress*, Sarayevo, 1979, p. 730.

Bocci, et al., Colorectal Administration of Human Interferon–Alpha, *International Journal of Pharmaceutics*, 1985, vol. 24, pp. 109–114.

Schafer, T., et al., Interferon Administered Orally: Protection of Neonatal Mice From Lethal Virus Challenge, *Science*, Jun. 23, 1972, vol. 176, pp. 1326–1327.

Hofmann, V.W., et al., Erste Erfahrungen bei der Behandlung von Virusbedington Kalberdurchfallen mit Gentechnisch Erzeugtem Interferon, *Dtsch. tierarztl. Wschr.*, vol. 92, pp. 278–280.

Phillpotts, R.J.; et al., Intranasal Lymphoblastoid Interferon ("Wellferon") Prophylaxis Against Rhinovirus and Influenza Virus in Volunteers, *Journal of Interferon Research*, 1984, 4:535–541.

Isacsoh, M.; Berson, B.; Sternberg, J.; Morag, A., Human Fibroblast Interferon in Treatment of Viral Diseases of the Skin and Mucous Membranes *Israel Journal of Medical Sciences*, 1983, vol. 19.

Cruz, et al., Protective Effect of Low–Dose Interferon Against Neonatal Murine Cytomegalovirus Infection, *Infection and Immunity*, Apr. 1981, pp. 332–342.

Yunde, H., et al., Effect of Radix Astragali Seu Hedysari on the Interferon System, *Chinese Medical Journal*, 1981, 94(I):35–40.

Arnaoudova, V., Treatment and Prevention of Acute Respiratory Virus Infections in Children with Leukocytic Interferon, *Rev. Roum. Med.—Virol*, 1976, 27, 2, p. 83–88.

Surkova, N.A., et al., Morphology of Immunogenesis In Aerosol Vaccination Against Measles Experimentally, 1970, article.

Annals of Internal Medicine, vol. 92, No. 1, (1981) "The Case of the Man Who Felt Too Well."

5 Agricultural Genetics Report (1986), Interferon Approved for Horse Use.

Amarillo Daily News, Section C, Oct. 25, 1985. "New product aims to combat effects of shipping fever".

Antosh, Nelson, Houston Chronicle, Dec. 30, 1984. Stafford firm will be first to market interferon–based product for cattle.

Aguet, Nature, 1980 284 459–461. High Affinity Binding of $^{125}$I–Labelled Mouse Interferon to a Specific Cell Surface Receptor.

Arnaoudova, et al., Arch. Immunologiae et Therapiae Experimentalis 731–736 (1977) Treatment and Prevention of Acute Viral, Respiratory Infections in Children with Leukocytic Interferon, 25.

Bechtol, et al., "Interferon Potential", Feedlot Health, The Drovers Journal Magazine, Sep. 1985.

Nature vol. 286 p. 110 (Jul. 10, 1980), Interferon Nomenclature.

Beef, Dec., 1984, New Interferon Product Approved in Texas to Control Shipping Fever.

Biotechnology News, Aug. 15, 1984.

Biotechnology, Oct. 1984, p. 841.

Borecky, Acta viral. 30: 161–169, 1986. Current View on the Perspectives of Interferon Therapy.

Cantell, K., Interferon 1979 vol. 1 (Ed. I. Gresser) Academic Press 1979 "Why is Interferon Not in Clinical Use Today?".

Cornett, The Drovers Journal Magazine, Oct. 1986. Interferon Tests Show Potential.

Cummins, et al., Abstract of "High Dose Oral, But Not Intraruminal, Human Interferon Alpha May Depress Feed Intake of Cattle," Abstract #11–17.

De Maeyer, Interferons and the Immune System, in Interferon, vol. 1: General and Applied Aspects—A. Billiau (ed.) pp. 167–185 (1984).

Ermolieva, H.M. et al., Journal Antibiotiki N12, pp. 1034–1039 (1967), Experimental Clinical Studies of Endogenous and Exogenous Interferons.

Dai Jia–Ziong, et al., Foreign Pediatrics Medical Annual 1983, 2—72–77 The Efficacy of Interferon in Common Pediatric Viral Infections.

Dai Jia–Ziong, et al., Chinese Pediatrics Journal, 1983, 21, 357–358., Preliminary Observations of aerosol Interferon in the Treatment of Viral Infections in Respiratory Tract.

Dainyak, L.B. et al., Vestnik Otolaryngology, pp. 59–61, N2 (Moscow 1977). Interferon Treatment of Chronic Tonsillitis.

Drobotko, L.N. et al., Stomatologia pp. 53–55, N1 1974. Treatment with Interferon Ointment of Acute Herpetic Stomatitis in Children.

Farr, B.M., et al., Antimicrobial Agents and Chemotherapy, 1984, 26 31–34, Intranasal Interferon–a2 for Prevention of Natural Rhinovirus Colds.

Feedlot Management, Aug. 1985, The Interferon Difference.

Flury, et al., Clinical Experiences with Interferon Therapy 1401–1405.

Fort Bend Business Journal, Jan./Feb. 1985, Stafford Firm Markets New Interferon–Based Drug.

Globe News, Amarillo, Texas (1984).

Goodman & Gilman, "The Pharmacological Basis of Therapeutics" 7th Edition; MadMillan Publishing Company, New York, 1985 pp. 5–9.

Greenberg, S.B. et al. Texas Rep. Biol. Med. 41:549–554 (1981) "Trials of Interferon in Respiratory Infections in Man".

Gresser, et al., Nature, 1974 251 543–545. "Pronounced Antiviral Activity of Human Interferon or Bovine and Procine Cells".

Igoshin, et al., Journal Vestnik Dermatoloty, Venrology (Moscow), vol. 10, Oct., pp. 41–43, 1983. Remote Results of Combined Therapy of Patients With a Psoriasis Using Interferon Inhalation.

Imanishi, et al.,Journal of Interferon Research, vol. I, Nov. 1980, 169–178, The Preventive Effect of Human Interferon–Alpha Preparation on Upper Respiratory Disease.

Billiau, Alfons, Interferon vol. 1 (Ed.) General and Applied Aspects (Ed. A. Billiau) Amsterdam: Elsevier, 23, 1984. "The Main Concepts & Achievements in Interferon Research: A Historical Account."

Isacsohn, M., et al., Israel Journal of Medical Sciences, 1983 19, 959–962, "Human Fibroblast Interferon in Treatment of Viral Diseases of the Skin and Mucous Membranes".

Jacobs, et al., Science 214: 1026–1028 (1981) "Intrathecal Interferon Reduces Exacerbations of Multiple Sclerosis".

Kajander, The Lancet (1979) 1, 984–985.

Levin, Isr. J. Med. Sc. 19 955–958 (1983) "Clinical Use of Interferon in Viral Infections".

Lotze, Michael, Treatment of immunologic disorders in AIDS, *AIDS* (DeVita et al., eds. 1985), pp. 235–263.

McGraw–Hill Concise Encyclopedia of Science & Technology, 1984.

The Merck Index, Merck & Co., Inc. 1983, 724–725.

Modern Horse Breeding, Jul. 1986, Alpha Interferon Shows Promise in Fighting Equine Respiratory Disease.

Paramonova, Treatment of Tonsillits of Viral Etiology by Interferon, Actual Problems of Otolaryngology (Proceedings), Tashkent 1978.

Paramonova, et al., Materials from Conference on the Study of Biosynthesis, Antimetabolites, and Chemotherapy of Viral Infections, Dec. 19–20, 1968, N8 (18).

Phillpotts, et al., Journal of Interferon Research 1984., 535–541 Intranasal Lymphoblastoid Interferon ("Wellferon"). Prophylaxis Against Rhinovirus and Influenza Virus in Volunteer.

Research News Report, The Texas Agricultural Experiment Station, The Texas A&M University System (Oct. 31, 1984).

Sanders, "Dorland's Illustrated Medical Dictionary" (1974), pp. 232, 1019, 1094, 1098, 1175–77.

Scott, D.M. & D.A.J. Tyrrell, Br. Med. J. 1568–1682 (1980) "Interferon: Therapeutic Fact or Fiction for the '80s".

Sisoeva, O.B., Transactions of the All Union Research Institute of Influenza (1972 Change of the Markers of Immune Status of Children Under the Influence of Interferon and Extract of Eleuterokokk, Prophylaxis of Influenza and Other Acute Respiratory Diseases in Children).

Soloviev, et al., Plenum Press NY 1073 pp 128–135, Interferon Theory and Application .

Streuli et al., Proc. Natl. Acad. Sci., 1981 78 2848–2852. Target Cell Specificity of Two Species of Human Interferon–Alpha Produced in *Escherichia coli* and of Hybrid Molecules Derived From Them.

Strustsovkaya, Journal Antibiotiki, vol. 20 #2, pp. 170–172. 1975. Experience with Use of Leukocytic Interferon and Metacyl in Children Suffering from Influenza.

Sun, Chong–Son et al., Journal of Interferon Research 1984, 449–459 Efficacy of Aerosolized Recombinant Interferons Against Vesicular Stomatitis Virus–Induced Lung Infection in Cotton Rats.

Tovey, et al., J. Gen. Virol., 1977 36 341–344. "Antiviral Activity of Bovine Interferons on Primate Cells".

Ulanovskaya, T.I. et al., Proceedings of Scientific–Practical Conference, Moscow (1971) Use of Leukocyte Interferon for Treatment and Prophylaxis of Acute Respiratory Diseases in Children of the First Months of Life.

Vander, et al., Human Physiology The Mechanisms of Body Function 1980, McGraw Hill 3rd Edition, 421–422.

Williams & Warwick, Gray's Anatomy, (36th Edition 1980). pp. 1267–131.

Yamamoto, et al., Journal of Interferon Research 1986, 143–152. Human Alpha– and Beta–Interferon But Not Gamma–Suppress the In Vitro Replication of LAV, HTLV–III and ARV–2.

Yonehara et al., J. Biol. Chem., 1983 258 (15) 9046–9049. Different Binding of Human Interferon $\alpha 1$ and $\alpha 2$ to Common Receptors on Human and Bovine Cells.

Yunde, Hou, et al., Chinese Medical Journal 1981 35–40.

WHO Technical Report Series No. 676 (1982) "Interferon Therapy".

Concise Medical Dictionary (Oxford 1985), pp. 82, 404, 433, 435, 470–471.

Fauci, The Acquired Immune Deficiency Syndrome: An Update, 102 Annals of Internal Medicine 800–813 (1985).

* cited by examiner

INTERFERON DOSAGE FORM AND METHOD THEREFOR

This application is a continuation of U.S. application Ser. No. 08/003,624 filed Jan. 13, 1993, now abandoned, which is a continuation of application Ser. No. 07/775,291, filed Oct. 9, 1991, now abandoned, which is a division of U.S. application Ser. No. 07/110,501, filed Oct. 26, 1987, now abandoned, which is a continuation-in-part of U.S. application Ser. No. 06/927,834, filed Nov. 6, 1986, now abandoned.

BACKGROUND OF THE INVENTION

This invention relates generally to an improved method of treating diseases of immuno-pathologic etiology in warm-blooded vertebrates using interferon in low oral dosages. This invention also relates to the use of interferon in low oral dosages to potentiate disease-corrective immune responses in warm-blooded vertebrates afflicted with immuno-resistant diseases characterized by apparent hyperactive or hypoactive immune system function.

"Interferon" is a term generically comprehending a group of vertebrate glycoproteins and proteins which are known to have various biological activities, such as antiviral, antiproliferative, and immunomodulatory activity at least in the species of animal from which such substances are derived. The following definition for interferon has been accepted by an international committee assembled to devise a system for the orderly nomenclature of interferons: "To qualify as an interferon a factor must be a protein which exerts virus nonspecific, antiviral activity at least in homologous cells through cellular metabolic processes involving synthesis of both RNA and protein." *Journal of Interferon Research*, 1, pp. vi (1980). "Interferon" as used herein in describing the present invention shall be deemed to have that definition.

Since the first descriptions of interferon by Isaacs and Lindeman [See, *Proc. Roy. Soc. London (Ser. B)*, Vol. 147, pp. 258 et seq. (1957) and U.S. Pat. No. 3,699,222], interferon has been the subject of intensive research on a worldwide basis. The literature is replete with publications concerning the synthesis of interferon, its proposed molecular characterizations, its clinical applications and proposed mechanisms of its antitumor, antiviral, and immune system activities.

Because of the intensity and disparate origins of research concerning interferon and its characteristics and uses, there exists a substantial lack of uniformity in such matters as classification of interferon types. There are also numerous, sometimes contradictory, theories concerning the mode of action of interferon in producing clinical effects.

Although originally isolated from cells of avian origin (chick allantoic cells), interferon production has been observed in cells of all classes of vertebrates, including mammals, amphibians, birds and reptiles. Interferon production by vertebrate cells is seldom spontaneous but is often readily "induced" by treatment of cells (in vivo or in vitro) with a variety of substances including viruses, nucleic acids (including those of viral origin as well as synthetic polynucleotides), lipopolysaccharides, and various antigens and mitogens.

Interferons have generally been named in terms of the species of animal cells producing the substance (e.g., human, murine, or bovine), the type of cell involved (e.g., leukocyte, lymphoblastoid, fibroblast) and, occasionally, the type of inducing material responsible for interferon production (e.g., virus, immune). Interferon has been loosely classified by some researchers according to induction mode as either Type I or Type II, with the former classification comprehending viral and nucleic acid induced interferon and the latter class including the material produced as a lymphokine through induction by antigens and mitogens. More recently, the international committee devising an orderly nomenclature system for interferon has classified interferon into types on the basis of antigenic specificities. In this newer classification, the designations alpha ($\alpha$), beta ($\beta$), and gamma ($\gamma$) have been used to correspond to previous designations of leukocyte, fibroblast, and type II (immune) interferons, respectively. Alpha and beta interferons are usually acid-stable and correspond to what have been called type I interferons; gamma interferons are usually acid-stable and correspond to what has been called type II interferons. The international committee's nomenclature recommendations apply only to human and murine interferons. *Journal of Interferon Research*, 1 pp. vi (1980).

In its earliest applications, interferon was employed exclusively as an antiviral agent and the most successful clinical therapeutic applications to date have been in the treatment of viral or virus-related disease states. It became apparent, however, that exogenous interferon was sometimes capable of effecting regression or remission of various metastatic diseases. An overview of current clinical trials of interferon as an antiviral and antiproliferative therapeutic agent is contained in *Interferon: In Vivo and Clinical Studies*, Volume 4, Eds: N. B. Finter and R. K. Oldham, Academic Press, New York, 1985.

The clinical agent of choice for the present invention is human leukocyte interferon, "mass-produced" by procedures involving collection and purification of vast quantities of human buffy coat leukocytes, induction with virus, and isolation from culture media.

In the work described above, interferon has been administered parenterally, i.e., intramuscularly and intradermally, with some successful topical and intranasal usages having been reported. It has seldom been administered intravenously because of substantial adverse effects attributable to "contaminants" in crude and even highly purified isolates.

As discussed above, there has been a significant research effort directed to the evaluation of therapeutic effects of interferon for a wide variety of diseases having an auto-immuno-pathologic basis. Before applicant's first report of successful oral administration of interferon in his U.S. patent application Ser. No. 415,525 (now U.S. Pat. No. 4,462,985), there was no recognition in the art of the potential offered by oral administration of interferon. The generally held belief was that interferon could not survive the digestive conditions of the upper alimentary canal.

Since applicant's first disclosure of the immunotherapeutic benefit achievable via oral administration of interferon of heterologous mammalian species, he has continued to investigate the efficacy of orally administered interferon. In U.S. Pat. No. 4,497,795, issued Feb. 5, 1985, applicant described and claimed the use of interferon administered orally or via intravenous administration to stimulate appetite and feed efficiency of bovine and porcine species. More recently applicant has described in now pending U.S. applications the use of interferon at dosages less than about 5 IU per pound of body weight for increasing feed efficiency and food utilization in warm-blooded vertebrates, for preventing and treating shipping fever, and for enhancing vaccine efficiency.

Human alpha-interferon has been marketed under the trademark Agriferon® by Immunomodulator Laboratories, Inc. ("IML") of Stafford, Tex. for veterinary use in Texas since Feb. 1985. The product is sold for oral administration to cattle to promote growth and feed efficiency and to prevent or treat viral respiratory infections. IML began selling an alpha-interferon product for horses in 1986. Both products are sold under a license of my U.S. Pat. No. 4,462,985.

SUMMARY OF THE INVENTION

Interferon contacting the oral and/or pharyngeal mucosa, in amounts of less than 5 IU/lb of body weight per day is consistently effective to potentiate disease-corrective immune responses in vertebrates afflicted with immuno-resistant disease states characterized by apparent hyperactive or hypoactive immune system function. Treatment in accordance with the present invention has been shown to effect remission of neoplastic disease, hyperallergenicity, immuno-resistant or immuno-debilitating viral infections and autoimmune disorders characterized by chronic tissue degenerative inflammation.

DETAILED DESCRIPTION OF THE INVENTION

The clinical agent of choice for use in the present invention is human leukocyte interferon (human alpha-interferon), "mass-produced" by procedures involving collection and purification of quantities of human buffy coat leukocytes, induction of interferon production with virus, and isolation of culture media. (See "Preparation of Human Alpha-Interferon" below.) Also acceptable for use in accordance with present intention are human alpha-interferon products produced by recombinant DNA technology and now commercially available from Schering-Plough (as Intron®) and Hoffmann-LaRoche (as Roferon®) and approved by the FDA for treatment (parenterally) of hairy cell leukemia of man. Such recombinant interferon products are believed to be particularly effective when used in combination. Gamma interferon is also available by recombinant technology and is presently undergoing clinical trials by Genentech and others. Fibroblast interferon (beta-interferon) can be prepared in accordance with Example 1 in applicant's U.S. Pat. No. 4,462,985 issued Jul. 31, 1984, the disclosure of which is hereby expressly incorporated by reference.

Interferon of human and murine origins has been quantified in the art in terms of International Units ("IU"). As used herein, a "unit" of interferon (to be distinguished from "IU") shall mean the reciprocal of a dilution of interferon-containing material that, as determined by assay, inhibits one-half the number of plaques of a challenge virus, the challenge virus being the vesicular stomatitis virus ("VSV"). So quantified a "unit" of interferon is routinely found to be about one-tenth the quantity of interferon represented by one "IU." In other words, for the purpose of defining the present invention, 1 unit ≈0.1 IU.

The present invention relates to an improved method of treatment of immuno-resistant disease states with interferon. The present invention is directed to the treatment of diseases in warm-blooded vertebrates, particularly certain diseases which the immune system of many species is poorly equipped to handle, as evidenced by either a lack of disease defeating response and/or an apparently misdirected immune response resulting in a chronic tissue degenerative inflammatory condition or other physical complications. While there has been a significant research effort directed to the use of interferon for treatment of such diseases, reported results, although positive overall, have been inconsistent. The principle reason for such inconsistency in view of my most recent research efforts is that earlier investigators have failed to define optimum dosage and route of interferon administration.

The present invention is based on applicant's discovery that interferon can be used as a consistently effective therapeutic agent for treatment of diseases having an immuno-pathologic basis—characterized by inadequate immune response and persistence of the disease or by an apparent hyperactive immune response resulting in tissue degenerative inflammatory conditions and related physical manifestations. Applicant has found that interferon, contacting the oral and pharyngeal mucosa in amounts from about 0.01 to about 5 IU/lb of body weight per day, is consistently efficacious for the treatment of diseases to which the immune system of many warm-blooded vertebrates does not effectively respond.

Disease conditions treated in accordance with the present invention include apparent autoimmune disorders characterized by a chronic tissue degenerative inflammatory condition. Diseases so characterized include multiple sclerosis, rheumatoid arthritis, stomatitis, and lupus erythematosus. Treatment of such disease is in accordance with the present invention comprises administering interferon at a dosage of 0.01 to about 5 IU/lb per day in a dosage form adapted to promote contact of said dosage of interferon with the oral and pharyngeal mucosa of said animal. Preferably, the dosage of interferon is from 0.1 to about 4.0 IU/lb per day, more preferably 0.5 to about 1.5 IU/lb of body weight per day. Alpha interferon, derived from tissue culture or by recombinant DNA techniques, is a preferred therapeutic agent in accordance with this invention. Some data have indicated better efficacy, i.e., a more pronounced immuno-modulatory effect, where the interferon is not homologous to the species being treated. Alpha interferon can be administered alone or in combination with beta interferon or gamma interferon.

It is critical that the interferon be administered in a dosage form adapted to assure maximum contact of the interferon in said dosage form with the oral and pharyngeal mucosa of the human or animal undergoing treatment. Contact of interferon with the mucosa can be enhanced by maximizing residence time of the treatment solution in the oral or pharyngeal cavity. Thus, best results seem to be achieved in human patients when the patient is requested to hold said solution of interferon in the mouth for a period of time. Contact of interferon with the oral and pharyngeal mucosa and thereafter with the lymphatic system of the treated human or animal is unquestionably the most efficient method administering immunotherapeutic amounts of interferon.

Another disease condition responding to treatment in accordance with the present invention is neoplastic disease. Thus, the administration of interferon in accordance with the above description can, alone or in combination with other drugs or therapy, help effect remission of cancers such as malignant lymphoma, melanoma, mesothelioma, Burkitt lymphoma and nasopharyngeal carcinoma and other neoplastic diseases, especially those of known or suspected viral etiology. Based on the results observed to date, it is believed that applicant's presently described method of treatment will similarly help effect remission of Hodgkin's Disease and leukemia.

Other disease conditions responding to treatment in accordance with the present invention are infectious diseases of viral origin in, for example, human, avian, porcine, canine and feline species. Significantly, viral infection typically exhibiting persistent resistance to treatment have shown a dramatic response to treatment with interferon in low doses contacting the oral and pharyngeal mucosa of infected patients. Beneficial results have been attained utilizing the present method to treat dogs having canine parvovirus and canine herpesvirus infections. Further, feline leukemia and feline infectious peritonitis have been shown to be particularly susceptible to treatment with alpha interferon and beta interferon in accordance with this invention.

Exemplary of human viral infections showing remarkable response to treatment in accordance with the present invention are infections of human rhinovirus (common cold), herpes simplex I virus (cold sores) and human papovavirus (warts). Based on treatment results to date, it is expected that contact of interferon at low dosage with the oral and pharyngeal mucosa will provide an effective treatment for Acquired Immune Deficiency Syndrome (AIDS) and disease conditions having the herpes simplex II virus as the causative agent. A patient experiencing a condition of viral myocarditis has responded favorably to the present treatment. Warts often dissipate within six to eight weeks after initiating treatment in accordance with this invention. Interferon administration in accordance with this invention can also be used to help prevent viral infections, for example, infections by the causitive agents of flus and colds, and to minimize the symptoms associated with such viral infections.

Other afflictions responding to contact of low dosage interferon are hyperallergenic conditions such as asthma. One "side effect" noted by patients treated in accordance with this invention is improved skin complexion. Thus, administration of interferon in dosages of about 0.01 to about 5 IU/lb of body weight per day is effective to treat acne, specifically and improve human skin complexion generally.

Further, stimulating the immune system by oral contact with low dosage interferon is believed to assist the body in fighting bacterial infection. Treatment in accordance with this invention alone or in combination with therapeutic amounts of antibiotics can be especially effective in knocking down infections of antibiotic resistant microorganisms.

Administration of interferon in accordance with the present invention is preferably continued until the symptoms of the disease condition being treated subside. This can range from a period of one day, for example, where a human rhinovirus is the disease causative agent, to a period of up to six months for treatment of neoplastic disease. Rheumatoid arthritis patients are pain free within 2 to 10 days of initiating treatment in accordance with the present invention. However, treatment of that disease is preferably conducted by administration of interferon for up to about three (3) months.

Daily dosage of interferon can be administered as a single dosage or, preferably, it is divided and administered in a multiple-dose daily regimen. A staggered regimen of at least one, for example, one to three days treatment per week or month, can be used as an alternative to continuous daily treatment.

Interferon can be administered in accordance with this invention in either a liquid (solution) or solid dosage form. Thus interferon can be administered dissolved in a buffered aqueous solution typically containing a stabilizing amount (1–5% by weight) of blood serums. Exemplary of a buffered solution suitable as a carrier of interferon administered in accordance with this invention is phosphate buffered saline prepared as follows:

A concentrated (20×) solution of phosphate buffered saline (PBS) was prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The solution is sterilized by autoclaving at 15 pounds pressure for 15 minutes and then diluted with additional water to a single strength concentration prior to use.

Alternatively the interferon can be formulated into flavored or unflavored solutions or syrups using a buffered aqueous solution of interferon as a base with added caloric or non-caloric sweeteners, flavor oils and pharmaceutically acceptable surfactant/dispersants.

It is also contemplated by the present invention to provide interferon in a solid dosage form such as a lozenge adapted to be dissolved upon contact with saliva in the mouth with or without the assistance of chewing. Such a unitary dosage form is formulated to release about 1 to about 1500 IU of interferon upon dissolution in the mouth for contact with the oral and pharyngeal mucosa. Thus a unitary dosage form of interferon in accordance with this invention can be prepared by art-recognized techniques for forming compressed tablets such as chewable vitamins. Similarly, interferon can be incorporated into starch-based gel formulations to form a lozenge which will dissolve and release interferon for contact with the oral mucosa when held in the mouth. Solid unitary dosage forms of interferon for use in accordance with the present invention can be prepared utilizing art recognized dosage formulation techniques. The pH of such formulations can range from about 4 to about 8.5. Of course, in processing to such unitary dosage forms one should avoid heating a pre-dosage form formulation, after addition of interferon, above about 50° Centigrade. Exemplary of a solid dosage form for animal use is a molasses block containing effective amounts of interferon.

Preparation of Human Alpha-Interferon

Human alpha-interferon can be prepared through the following procedure, commonly referred to as the Cantell procedure. The process begins with packs of human leukocytes, obtained in this case from the Gulf Coast Regional Blood Center, Houston, Tex. The buffy coats in these packs are pooled into centrifuge bottles, and then are diluted with 0.83% ammonium chloride. The mixture is incubated for 15 minutes with intermittent shaking, and is then centrifuged for 20 minutes at 2000 rpm. The supernatant is discarded, and the cell pellets are resuspended with a minimal volume of sterile phosphate buffered saline (PBS). The mixture is then diluted with ammonium chloride and centrifuged. The supernatant is again discarded, and the remaining cell pellets are resuspended with a minimal volume of a tissue culture medium such as Minimal Essential Medium (MEM), available from KC Biological. The cell concentration is determined with a Coulter counter.

Interferon induction takes place in glass or plastic bottles. The induction medium contains MEM, 75 mM Hepes (available from Calbiochem), 75 mM Tricine (available from Sigma Chemical Co.), human agamma serum (18 mg/ml), and gentamycin sulfate (from M.A. Bioproducts; 50 mcg/ml). The cells are added to the induction vessels at a final concentration of about 5 to 10 million cells per milliliter. The induction vessel is incubated in a 37° C. water bath, and interferon alpha is added as a primer.

After two hours, Sendai virus is added to the induction mixture. This causes alpha interferon to be produced in the supernatant by the leukocytes. After a 12–18 hour incubation time, the induction mixture is centrifuged. The cells are discarded, and the supernatant is then purified.

The crude interferon is chilled to 10° C. or below in an ice bath. Five molar potassium thiocyanate is added to obtain a final concentration of 0.5M. This solution is stirred for 15 minutes, and then its pH is lowered to 3.3 by adding hydrochloric acid. The mixture is then centrifuged at 2800 rpm for 30 minutes, and the supernatant is discarded.

The pellets are then resuspended in 95% ethanol and are stirred for 15 minutes. This suspension is centrifuged at 2800 rpm for 20 minutes, and the pellets are discarded. The pH of the supernatant is then adjusted to 5.8 with sodium hydroxide. The mixture is stirred for 10 minutes, and then centrifuged at 2800 rpm for 20 minutes. The pellets are discarded. The pH of the supernatant is then adjusted to 8 with sodium hydroxide. This solution is stirred for 10 minutes, followed by centrifugation at 2800 rpm for 20 minutes. The supernatant is discarded, and the pellets are resuspended with 0.5M potassium thiocyanate in a 0.1M sodium phosphate buffer. This suspension is stirred at 4° C.

Next, the suspension is centrifuged at 2800 rpm for 20 minutes, and the pellets are discarded. The pH of the supernatant is adjusted to 5.3 with hydrochloric acid. After stirring for 10 minutes and centrifugation, the pH of the supernatant is adjusted to 2.8 with hydrochloric acid, followed by further stirring for 20 minutes. This mixture is centrifuged at 2800 rpm, and the resulting pellet is purified human alpha-interferon.

The pellet is resuspended with 0.5M potassium thiocyanate in 0.1M sodium phosphate buffer, having a pH of 8.0. It is then dialyzed against PBS at 4° C., with two changes of PBS. This mixture is then centrifuged and the precipitate is discarded. The remaining purified alpha interferon is sterilized by filtration through a 0.2 micron filter. A human alpha-interferon is produced in accordance with this procedure by Immuno Modulators Laboratories, Inc., Stafford, Tex., and sold under the trademark Agriferon® for use in cattle and Equiferon® for use in horses.

Other procedures known to those skilled in the art are available for making interferons, such as human alpha-interferon and human gamma-interferon. For example, U.S. Pat. Nos. 4,376,821 and 4,460,685 disclose methods of making human gamma-interferon. A method of making bovine fibroblast (beta) interferon is disclosed in applicant's U.S. Pat. No. 4,462,985.

CLINICAL STUDIES

Tables 1–4 below summarize the results of clinical studies of the administration of interferon by veterinarians orally to 137 dogs and cats as of November, 1985. The studies were conducted with both human alpha-interferon and bovine beta-interferon. Tables 1–4 compare survival rates of pets with feline leukemia virus-associated diseases or canine parvovirus disease. Unequal numbers of pets were treated with each type of interferon; bovine beta-interferon was given to 78 pets and human alpha-interferon was given to 59 pets.

Bovine beta-interferon was produced in flasks of confluent monolayers of bovine fetal kidney (BFK) cells. Culture supernatant was harvested 24 hours after bluetongue virus induction of BFK cells. The supernatant was dialyzed 24 hours in a pH 2.0 buffer and for another 24 hours in a PBS (pH 7.4) buffer before interferon assay. Procedures for the assay and characterization of bovine beta-interferon were essentially as described by Rosenquist and Loan, *American Journal of Veterinary Research*, 28; 619–628, 1967. Interferon titers as "units" were expressed as the reciprocals of the dilutions that provided a 50% reduction in the number of VSV plaques as compared with the number in control cultures. The BFK cell culture interferon produced by this method had an average titer of 7,000 units per milliliter. Dogs were given bovine beta-interferon, 5–10 ml/dose, as least three times/day after a diagnosis of CPV disease. Cats positive by ELISA for feline leukemia virus and exhibiting clinical signs of disease were given 1 ml/10 lb of body weight 2–3 times daily for five days. After a five-day interval, cats were retreated at least once for another five days.

Human alpha interferon was obtained from IML, Inc. of Houston, Tex. Cases were treated with lot AO26 applied at $6 \times 10^6$ IU/ml. Lot AO26 of human alpha interferon was diluted 1:150 in Eagles' minimum essential medium (MEM) and used as the stock solution from which 1 ml was further diluted 1:1000 with 1 liter of MEM for treatment. The usual dose of human alpha interferon was 4 IU/lb body weight given at least three times daily after a diagnosis of CPV disease was made. For feline leukemia, cats were treated with human alpha-interferon 2–3 times daily for five days as reported for bovine beta-interferon.

Significantly (P<0.05) more cats lived six and twelve months after diagnosis and treatment for feline leukemia virus if alpha-interferon was given, compared to treatment with bovine beta-interferon. Significantly (P<0.05) more dogs survived CPV disease when given alpha interferon (92%) compared to those dogs given bovine beta-interferon (69%).

TABLE 1

Summary of Survival Date from clinically ill cats positive for FeLV.

| Treatment | Months After Treatment | | |
|---|---|---|---|
| | 1 | 6 | 12 |
| Human alpha-IFN | 25/33 | 21/32* | 19/31* |
| Bovine IFN | 26/36 | 15/36 | 13/36 |

Numerator = no. alive; denominator = no. treated.
*Cats given human alpha-IFN had significantly (P < .05) higher survival rates at 6 and 12 months after treatment than cats given bovine IFN. Significance was determined by Chi Square test.

TABLE 2

Percent survival of clinically ill cats positive for FeLV.

| Treatment | Months After Treatment | | |
|---|---|---|---|
| | 1 | 6 | 12 |
| Human alpha-IFN | 76% | 66%* | 61%* |
| Bovine IFN | 72% | 42% | 36% |
| Historical Control | <50% | <30% | — |

Numerator = no. alive; denominator = no. treated.
*Cats given human alpha-IFN had significantly (P < .05) higher survival rates at 6 and 12 months after treatment than cats given bovine IFN. Significance was determined by Chi Square test.

TABLE 3

Response of CPV disease to treatment with bovine
interferon or human alpha-interferon, by veterinarian.

| Attending Veterinarian | Bovine IFN Beta | | Human Alpha IFN | |
|---|---|---|---|---|
| | Lived | Died | Lived | Died |
| S | 16/21 | 5/21 | 14/16 | 2/16 |
| M | 6/11 | 5/11 | 7/7 | 0/7 |
| R | 7/10 | 3/10 | 3/3 | 0/3 |
| | 29/42 (69%) | 13/42 (31%) | 24/26 (92%) | 2/26 (8%) |

Dogs treated with human alpha-interferon had a significantly (P<0.05) higher survival rate compared to dogs treated with bovine IFN. Significance between groups was determined by Chi Square test.

TABLE 4

Treatment days for CPV disease.

| Treatment | No. of Days | Average No. Treatment Days* | SD** | Survival Rate |
|---|---|---|---|---|
| Bovine IFN | 42 | 3.31 | 1.95 | 69% |
| Human alpha IFN | 26 | 2.75 | 0.92 | 92% |

*Calculated on surviving dogs only.
**Standard deviation of the mean treatment days.

Canine Herpesvirus Challenge of Newborn Dogs

Canine herpesvirus infection of dogs less than one week of age are invariably fatal, but older pups usually survive. Interferon has been successfully used to treat viral infections of many species. These studies were conducted to assess the efficacy of interferon in canine herpesvirus (CHV) inoculated puppies.

Five (5) pregnant bitches were obtained from a USDA licensed supplier and were housed in a USDA approved research facility in Canyon, Tex. After the pups whelped, they were inoculated with 6.3 log 10 units of virulent CHV obtained from Dr. Richard Mock of the Texas A&M University Veterinary Medical Diagnostic Laboratory (TVMDL) in Amarillo, Tex. Human alpha-interferon (HAI) or placebo was given to pups orally as treatment in an effort to increase the survival rate of the CHV inoculated pups. Each litter was divided into control and treated animals. The procedures and schedule for each litter are discussed below. All dead animals were necropsied at TVMDL, Amarillo, Tex.

Litter 1

Nine (9) pups were inoculated orally with CHV on the day of birth. Interferon was given at 6–10 units (1×), or ten times the dosage at 60–100 units (10×). Three pups were given 0.5 ml placebo, 3 pups were given 0.5 ml HAI (1×), and 3 pups were given 0.5 ml of a 10× concentrate of HAI orally twice daily for 7 days (if they lived that long). The 3 controls died 5, 6, and 8 days after CHV inoculation. The 3 pups given HAI (1×) lived 7, 7, and 9 days and the 3 pups given 10× HAI lived 6, 7, and 7 days after CHV inoculation.

Pups given HAI (1×) lived an average of 1.3 days longer than controls, but the longer survival time was not statistically significant. The higher dosage, HAI (10×), did not provide a survival benefit over the lower dosage, but instead pups given the higher dosage died, on the average, one day sooner.

Litter 2

Eight (8) pups were inoculated with CHV orally 2 days after birth. Interferon was given at 6–10 units (1×), or ten times the dosage (1×), or 1/10th the dosage (1/10×). All interferon was given orally after dilution in PBS. Two (2) pups were given 0.5 ml PBS, 2 were given 0.5 ml HAI at 1/10th concentration, 2 were given HAI (1×), and 2 were given a 10× concentrate of HAI. All treatments were given orally twice daily for 5 days starting 1 day before CHV inoculation. The 2 controls died <1 and 9 days after CHV inoculation and the HAI treated (1/10th dose, full dose, 10× dose) pups died 8 and 9, 5 and 9, 8 and 8 days after CHV inoculation, respectively.

No benefit from treatment at any dosage was seen. The death of a control pup within a day after CHV inoculation was probably not related to CHV inoculation.

Litter 3

Nine (9) pups were inoculated with CHV orally 3 days after birth. Two pups were given 0.5 ml PBS, 2 were given 0.5 ml HAI (1×), 2 were given 1/10th dose HAI, and 3 were given 2 IU of recombinant human alpha-interferon from Schering-Plough. All treatments were given orally twice daily for 5 days starting two days before CHV inoculation. Both pups given HAI (1×) survived until necropsied 19 days after CHV inoculation. One control pup died 14 days after CHV inoculation and 1 survived until necropsied 19 days after CHV inoculation. Pups given 1/10th dosage of HAI died 8 and 13 days after CHV inoculation. Only one pup given recombinant human alpha-interferon died (12 days after CHV); the other 2 pups survived until necropsied 19 days after CHV inoculation.

These pups, inoculated 3 days after birth, did not develop an overwhelming CHV infection (only 1 of 2 controls died). A 1/10th dose of HAI did not protect either pup but both HAI (1×) treated pups survived.

Litter 4

Fourteen (14) pups were inoculated orally with CHV 2 days after birth. Seven (7) pups were given PBS and 7 pups were given HAI (1×) orally twice daily for 7 days (if they lived that long) starting 2 days after CHV inoculation. The 7 controls died 1, 5, 7, 8, 8, 9, and 9 days after CHV inoculation. One of the HAI (1×) treated pups survived and the other 6 pups died 1, 6, 8, 9, 9, and 12 days after CHV inoculation. The deaths of 2 pups only 1 day after CHV inoculation were probably not related to CHV inoculation.

One HAI (1×) treated pup lived 3 days beyond the last surviving control and one HAI (1×) treated pup lived 2 weeks (until necropsied) beyond any treated control pup. Average survival time of interferon treated pups was longer than control survival time, but not significantly so.

Litter 5

Six (6) pups were inoculated orally with CHV 2 days after birth. Three (3) pups were given PBS and 3 were given HAI (1×) orally once daily starting 5 days after CHV inoculation. The 3 controls died 6, 6, and 7 days after CHV inoculation. One of the HAI (1×) treated pups survived (until necropsied) and the others died 8 and 9 days after CHV inoculation.

All interferon treated pups lived longer than any of the control pups. Treatment with HAI (1×) did not begin until 5 days after CHV inoculation, yet survival was significantly (P<0.05) prolonged.

In summary, on the average, puppies treated with human alpha-interferon had longer survival times and enhanced survival rates compared to littermate controls, after canine herpesvirus challenge. A total of 7 puppies (1 control and 6 interferon treated) survived the normally fatal CHV inoculation. The data is summarized in the Table 5 below.

TABLE 5

Summary of Canine Herpesvirus Data

| Litter | No. of Pups | Dosage | Average * Survival Time (Days) | Survivors |
|---|---|---|---|---|
| 1 | 3 | control | 6.33 | 0 |
| 1 | 3 | HAI 1X | 7.67 | 0 |
| 1 | 3 | HAI 10X | 6.67 | 0 |
| 2 | 2 | control | 4.5** | 0 |
| 2 | 2 | HAI 1/10th | 8.5 | 0 |
| 2 | 2 | HAI 1X | 7.0 | 0 |
| 2 | 2 | HAI 10X | 8.0 | 0 |
| 3 | 2 | control | 14.0 | 1 |
| 3 | 2 | HAI 1/10th | 10.5 | 0 |
| 3 | 2 | HAI 1X | — | 2 |
| 3 | 3 | recombinant IFN | 12.0 | 2 |
| 4 | 7 | control | 6.7 | 0 |
| 4 | 7 | HAI 1X | 7.5 | 1 |
| 5 | 3 | control | 6.3 | 0 |
| 5 | 3 | HAI 1X | 8.5 | 1 |

* dead dogs survival time; living puppies not calculated.
**includes one pup living only one day beyond CHV inoculation.

Treatment of Nasal Solar Dermatitis

Three cases of nasal solar dermatitis (collie nose) cleared after human alpha-interferon treatment of 1 unit/lb body weight orally and topical treatment (a few ml at 20 units/ml).

Treatment of Canine Lupus Erythematosus

Two cases diagnosed as canine lupus erythematosus were cured by human alpha-interferon treatment. A 2 year-old Lhasa apso male had been treated with prednisolone for 1 year for 3 dermatological lesions on the abdomen and prepuce. The flat glistening lesions were continually licked by the dog. Within 1 week of oral human alpha-interferon treatment (1 unit/lb body weight daily for 5 days, then after 1 week, treatment was repeated for 5 days) 2 lesions completely healed and the third lesion was reduced to ½ its original size. Within 4 weeks, the lesions were all completely healed and all therapy ceased. One year later, a skin lesion reappeared but promptly healed after interferon treatment was repeated. The skin lesions have not reappeared in the past 10 months.

A 6 year-old spayed female Chihuahua cross had a spider shaped (4 cm by 2 cm approximately) skin lesion on the abdomen. The lesion was flat, glistening and pruritic. Six weeks of prednisolone treatment resulted in complete healing. The following summer, the lesion reappeared and was treated with oral human alpha-interferon at about 1 unit/lb body weight daily for 5 days. Within 5 days the lesion was reduced to ⅓ its original size and completely disappeared within 10 days. The lesion has not reappeared in the past year.

Treatment of Feline Infectious Peritonitis

Table 6 shows the results of 17 cases of feline infections peritonitis (FIP) as diagnosed by practicing veterinarians. Human alpha-interferon (IFN) treatment resulted in a significantly greater survival rate than treatment with bovine beta-IFN.

TABLE 6

Survival of clinically ill cats diagnosed as FIP

| Treatment | No. Cats Treated | Alive | Dead | Survival Rate |
|---|---|---|---|---|
| Human alpha-IFN | 11 | 10 | 1 | 91% |
| Bovine beta-IFN | 6 | 3 | 3 | 50% |
| Total | 17 | 13 | 4 | 76% |

Cats given human alpha-IFN had a significantly (P=0.0574) greater survival rate than cats given bovine beta-IFN.

Human Treatment with Exogenous Human Alpha-Interferon

Human patients were treated with human alpha-interferon in the therapy of acute rheumatoid arthritis, multiple sclerosis, asthma, acne, malignant lymphoma, mesothelioma, and apthous stomatitis. Therapy consisted of oral administration of 0.7 IU per lb. of patient body weight twice daily, once in the morning and once in the evening. None of the patients noted any fever or anorexia associated with the administration of alpha interferon. Interferon was administered in a buffered solution having a concentration such that a single dosage could be administered in a volume of about 1 to about 20 ml of liquid. Each patient generally retained the interferon solution in his mouth for a period of time up to about one minute. After that time the solution was either swallowed or discharged from the patient's mouth.

Two patients suffering from rheumatoid arthritis were treated—a Caucasian male age 44 and a Caucasian female age 44. The male patient was pain free in 7 days, and the female was pain free in 10 days. They were both continued on the oral interferon for 21 days total and have remained asymptomatic.

It has been found that recurrence of a treated arthritic condition can be minimized if treatment in accordance with the present invention is continued over a period of up to about three months.

A 30-year-old Caucasian female nurse afflicted with multiple sclerosis and who had had an extensive neurologic workup at City of Hope Hospital in Los Angeles received treatment in accordance with the present invention for 21 days. The patient has had no recurrence of her neurologic symptoms for the past nine months.

A 42-year-old Caucasian male diagnosed to have a malignant lymphoma had completed chemotherapy with dismal results and was considered terminal. He was treated for three weeks with oral interferon. Six months after starting treatment he was released by his oncologist as free of the disease.

An 82-year-old Caucasian female was diagnosed to have mesothelioma. Presently there is no effective treatment for that disease and only a 9-month average survival rate is predicted. During her treatment with human alpha-interferon she had thoracentesis on two occasions for plural effusion. Otherwise, the patient has been active and has survived for 43 months.

A 32-year-old Asian male with apthous stomatitis was treated for two weeks with human alpha-interferon in accordance with the present invention. There has been no recurrence of the ulcers over the last six months since treatment was completed.

BKC is a 29 year-old Caucasian female and KKJ is a 20 year-old Caucasian female. Both are afflicted by acne-like skin blemishes at the time of their monthly menstrual cycle. Oral human alpha-interferon given at about 1 unit/lb of body weight for 3 days prior to the time of their cycle reduces the severity and number of skin blemishes.

Treatment of Warts in Humans with Bovine Alpha-Interferon

MAH, a 38 year-old Caucasian Caucasian female, had 7 warts on the middle finger of her right hand. After 9 months duration, medical treatment was sought, and liquid nitrogen was applied by a dermatologist. Only one wart on the finger regressed after treatment. Three warts coalesced to create a large wart area that, over the next year, acquired a roughly 12 millimeter square shape. Oral bovine alpha interferon treatment was started at a dosage of 6 ml daily for 6 consecutive days. The concentration of alpha-interferon was 30 units/ml; it was derived from the nasal secretions of cattle infected with infectious bovine rhinotracheitis virus. All the warts completely regressed within 6 weeks of the first dose of interferon.

Interferon Dosage Formulations (1) Lozenge

A starch gel-based lozenge containing interferon is prepared by combining 150 grams of sucrose, 550 ml phosphate buffered saline, and 250 grams of a cold-water-soluble starch such as that described in U.S. Pat. No. 4,465,702, heating that mixture with stirring to a temperature of about 75° C., cooling the mixture to about 30° C. and thereafter blending into the paste-like mass 50 ml of phosphate buffered saline PBS containing human alpha interferon at a concentration of 250 IU/ml. The mixture is then formed into multiple portions of about 5 to about 10 grams each which set upon standing under drying conditions to a starch candy gel-like consistency. The lozenges thereby produced can be administered to a patient singly or in combination. The patient is instructed to hold the lozenge in his mouth until it is completely dissolved to release the interferon component for contact with the oral mucosa.

(2) Chewable Vitamin

A chewable vitamin formulation is prepared, for example, according to the description of U.S. Pat. No. 3,857,939 by coating one or more components thereof prior to tableting with an interferon solution in an amount sufficient to provide about 1 to about 1500 units of interferon in each chewable vitamin tablet.

(3) Mouthwash

A mouthwash formulation is prepared in accordance with the present invention by combining 850 ml PBS, 100 ml of glycerin, 50 grams of dextrose, and a mixture of 0.3 ml of a flavor oil pre-mixed with 30 ml of a palatable, pharmaceutically acceptable surfactant/dispersant having an HLB from about 15 to about 25 and 50 ml of a PBS solution of interferon (concentration 120 IU/ml). The formulation contains interferon at a concentration of about 120 IU per 20 ml dosage. The patient is asked to hold a 20 ml volume of the mouthwash in his mouth, optionally gargling with the same, for a period of about 15 seconds to about one minute.

(4) Syrup

Interferon is added to a commercial cough syrup formulation in an amount sufficient to provide an interferon containing syrup formulation having about 1 to about 1500 IU of human interferon per tablespoon of syrup.

(5) Effervescent Tablet

A tableting mixture comprising a pharmaceutically acceptable alkali metal carbonate or bicarbonate, an organic acid such as citric acid, human interferon (preferably dispersed on a suitable organic or inorganic carrier therefor) in an amount sufficient to provide a per tablet dose of about 1 to about 1500 units of interferon per dose, and further including suitable tableting excipients such as lubricants and binders, is compressed into a unitary dosage form of interferon. The compressed tablet effervesces upon contact with water to release interferon to the resulting buffered solution. The dosage of interferon is readily available in solution for contact with the oral pharyngeal mucosa of a patient in need of said dosage of interferon.

What is claimed is:

1. A solid immunotherapeutic lozenge dosage form of interferon for human use, said dosage form comprising about 1 to about 1500 IU of alpha-interferon and a saliva soluble pharmaceutically acceptable carrier selected so that said lozenge dosage form dissolves completely during contact with saliva in the mouth to provide the interferon in saliva solution and to deliver interferon through the oral and pharyngeal mucosa.

2. The lozenge dosage form of claim 1 formed as a compressed tablet.

3. A method of preparing a dosage form of interferon for use by human patients to stimulate a systemic immunotherapeutic response, said method comprising the step of combing interferon and a pharmaceutically acceptable, solid carrier to form a mixture, and forming said mixture into a lozenge containing about 1 to about 1500 IU of alpha-interferon per lozenge, said lozenge characterized by its complete dissolution in saliva in a patient's mouth to form a saliva solution of the carrier and the interferon and to deliver interferon through the patient's oral and pharyngeal mucosa.

4. The method of claim 3 wherein the interferon used to prepare the lozenge is alpha-interferon.

5. The method of claim 3 wherein the lozenge is formed from the mixture of interferon and solid carrier by compressing the mixture into tablet form.

6. A solid immunotherapeutic dosage form of interferon for delivery of interferon to the lymphatic system of a patient to stimulate a systemic immunotherapeutic response, said dosage form comprising alpha-interferon and a solid carrier, said solid immunotherapeutic dosage form characterized by is complete dissolution during contact with saliva to provide a saliva solution of the carrier and the interferon in the mouth and to deliver the interferon through the oral and pharyngeal mucosa and into the patient's lymphatic system.

7. The dosage form of claim 6 wherein the solid dosage form is a lozenge dosage forms.

\* \* \* \* \*